United States Patent [19]

Gatti et al.

[11] Patent Number: 5,091,373
[45] Date of Patent: * Feb. 25, 1992

[54] METHOD OF TREATING TUMORS WITH A PHARMACEUTICAL COMPOSITION CONTAINING ANTHRACYCLINE GLYCOSIDES

[75] Inventors: Gaetano Gatti, Sesto San Giovanni; Diego Oldani, Robecco sul Naviglio; Carlo Confalonieri, Cusano Milanino; Luciano Gambini, Cornaredo, all of Italy

[73] Assignee: Farmitalia Carlo Erba S.r.l., Milan, Italy

[*] Notice: The portion of the term of this patent subsequent to Feb. 25, 2009 has been disclaimed.

[21] Appl. No.: 590,536

[22] Filed: Sep. 28, 1990

Related U.S. Application Data

[63] Continuation of Ser. No. 455,764, Dec. 28, 1989, abandoned, which is a continuation of Ser. No. 331,078, Mar. 28, 1989, abandoned, which is a continuation of Ser. No. 890,478, Jul. 30, 1986, abandoned, which is a continuation of Ser. No. 788,158, Oct. 16, 1985, Pat. No. 4,675,311.

[30] Foreign Application Priority Data

Oct. 22, 1984 [GB] United Kingdom ............... 8426672

[51] Int. Cl.⁵ ............................................. A61K 31/70
[52] U.S. Cl. ..................................... 514/34; 536/6.4; 514/788; 514/789
[58] Field of Search ..................... 514/34, 788, 789

[56] References Cited

U.S. PATENT DOCUMENTS

| | | | |
|---|---|---|---|
| 4,039,663 | 8/1977 | Arcamone et al. | 514/34 |
| 4,112,076 | 9/1978 | Arcamone et al. | 514/34 |
| 4,166,848 | 9/1979 | Bernardi et al. | 536/6.4 |
| 4,325,947 | 4/1982 | Penco et al. | 514/34 |
| 4,355,026 | 10/1982 | Umezawa et al. | 514/34 |
| 4,438,105 | 3/1984 | Suarato et al. | 514/34 |
| 4,522,815 | 6/1985 | Bargiotti et al. | 514/34 |
| 4,526,960 | 7/1985 | Broadhurst et al. | 536/6.4 |
| 4,537,882 | 8/1985 | Horton et al. | 514/34 |
| 4,550,159 | 10/1985 | Umezawa et al. | 514/34 |

FOREIGN PATENT DOCUMENTS

| | | | |
|---|---|---|---|
| 1161278 | 8/1969 | United Kingdom | 536/6.4 |
| 2124224 | 2/1984 | United Kingdom | 536/6.4 |

OTHER PUBLICATIONS

Jones, "Current Concepts in the Use of Doxorubicin Chemotherapy" 1982, pp. 28, 40, 51, 59, 61–66, 74, 79, 90–91, 98, 99, 107, 108 and 119.
Pratt et al., "Am. J. Dis. Child", vol. 127, Apr. 1974, pp. 534–536.
Tan et al., "Cancer", vol. 32, Jul. 1973, pp. 9–17.
Bonadonna et al., "Cancer Research", vol. 30, Oct. 1970, pp. 2572–2582.
Chemical Abstracts, vol. 104, No. 6, Feb. 10, 1986, p. 382, No. 39716d Columbus, Ohio, & JP-A-60 92 212 (Kyowa Hakko Kogyo Co. Ltd.) 23-05-1985.

*Primary Examiner*—Johnnie R. Brown
*Assistant Examiner*—Elli Peselev
*Attorney, Agent, or Firm*—Armstrong, Nikaido, Marmelstein, Kubovcik & Murray

[57] ABSTRACT

Stable, rapidly soluble, lyophilized injectable preparations comprising an anthracycline glycoside, or a pharmaceutically acceptable salt thereof, as the active drug substance, and use of said preparations in the treatment of tumors.

8 Claims, No Drawings

METHOD OF TREATING TUMORS WITH A PHARMACEUTICAL COMPOSITION CONTAINING ANTHRACYCLINE GLYCOSIDES

This application is a continuation of application Ser. No. 07/455,764 filed Dec. 28, 1989, now abandoned, which is a continuation of Ser. No. 07/331,078 filed Mar. 28, 1989, now abandoned, which is a continuation of Ser. No. 06/890,478 filed July 30, 1986, now abandoned, which is a continuation of apllication Ser. No. 06/788,158 filed Oct. 16, 1985, now U.S. Pat. No. 4,675,311.

The present invention relates to stable, rapidly soluble, lyophilised injectable preparations comprising an anthracycline glycoside, or a pharmaceutically acceptable salt thereof, as the active drug substance, and to the use of said preparations in the treatment of tumours.

The lyophilised compositions of the invention are characterised by comprising, in addition to the active drug substance, a cosolubilising agent which is able to enhance the solubility of the lyophilised cake when this is reconstituted, particularly when reconstitution is made with physiological saline solution.

It is currently known that reconstitution with sterile physiological saline solution is preferable, rather than reconstitution with sterile water, in order to obtain isotonic reconstituted injectable solutions, i.e. solutions having a tonicity more compatible with that of the blood.

It is also known that solubility problems are sometimes encountered in reconstitution, particularly with physiological saline solution, of certain anthracycline glycoside-containing freeze-dried preparations, because the lyophilized cake dissolves somewhat slowly and complete dissolution may require prolonged shaking.

The problem is of particular relevance in view of the recognised toxicity of drugs of the anthracycline glycoside family. It has now been found that the presence of a suitable cosolubilising agent in a lyophilised anthracycline glycoside-containing preparation enhances to a great extent the solubility of the drug so that upon reconstitution, e.g. with physiological saline solution, but also with sterile water, complete dissolution is achieved in a few seconds without any difficulty.

The anthracycline glycoside active drug substance in the pharmaceutical compositions of the invention may be any anthracycline glycoside, for example one of those disclosed in the UK Patent Specifications Nos. 1161278, 1217133, 1457632, 1467383, 1500421 and 1511559. In particular, the said anthracycline glycoside is, for example, doxorubicin, 4'-epi-doxorubicin (i.e. epirubicin), 4'-desoxy-doxorubicin (i.e. esorubicin), daunorubicin and 4-demethoxy-daunorubicin (i.e. idarubicin).

The cosolubilising agent used as solubility enhancer in the preparation of the invention is a compound selected from the group consisting of a hydroxy-, mercapto-or amino-benzoic acid, for example p-hydroxy- or o-hydroxy-or p-amino-benzoic acid, an alkali-metal salt thereof, for example a sodium or potassium salt, a $C_1$-$C_4$ alkylester thereof, for example a methyl-, ethyl-, propyl- or butyl ester, a ring-halogenated methyl-substituted phenol, for example 3-methyl-4-chlorophenol or 3,5-dimethyl-4-chlorophenol; an amino acid, in particular a neutral amino acid, for example a neutral aliphatic amino acid such as e.g. glycine, alanine, leucine and the like, a neutral thioaliphatic amino acid such as e.g. cysteine or methionine, a neutral aromatic amino acid such as e.g. phenylalanine or tyrosine or a neutral heterocyclic amino acid such as e.g. proline or hydroxyproline; or a combination of two or more of the above said compounds.

Some of the above cosolubilising agents are known to be used as preservatives/bacteriostatics in pharmaceutical formulations but there is nothing known about their possible role as solubility enhancers in reconstitution of lyophilised preparations, e.g. anthracycline glycoside-containing preparations. For example, K. P. Flora et al (*J. Pharm. Pharmacol.* 1980, 32:577) report about freeze-drying of doxorubicin hydrochloride formulations containing 4 parts of p-hydroxy-benzoic acid methyl ester and 1 part of p-hydroxy-benzoic acid propyl ester as a preservative, but not a single indication is given there of a possible role of said preservatives in improving the solubility of the freeze-dried preparation. Furthermore there isn't any evidence in the article of Flora et al that the solutions used for the freeze-drying process may be suitable for injection. As is known, in fact, solutions for injection must be sterile, in particular aqueous solutions are obtained from a lyophilised preparation by dissolving it in sterile, pyrogen-free water for injection, while this does not result in the case of the Flora's solutions.

Accordingly, the invention provides a stable, rapidly soluble, lyophilised injetable preparation comprising and anthracycline glycoside, or a pharmaceutically acceptable salt thereof, and a cosolubilising agent which is a hydroxy-, mercapto- or amino-substituted benzoic acid, or an alkali metal salt thereof or a $C_1$-$C_4$ alkyl ester thereof, or a ring-halogenated methyl-substituted phenol or an amino acid, or a combination of two or more of said compounds, excluding preparations wherein the anthracycline glycoside is doxorubicin hydrochloride and, at the same time, the cosolubilising agent is a combination of 4 parts of p-hydroxy-benzoic acid methyl ester and 1 part of p-hydroxy-benzoic acid propyl ester.

In the preparations of the invention the anthracycline glycoside and the cosolubilising agent may be any of those previously indicated. A preferred anthracycline glycoside is, in particular, doxorubicin, 4'-epi-doxorubicin, 4'-desoxy-doxorubicin, daunorubicin or 4-demethoxy-daunorubicin, or a pharmaceutically acceptable salt thereof.

The preferred cosolubilising agent is either a compound selected from the group consisting of p-hydroxy-benzoic acid and the methyl ester thereof, p-amino-benzoic acid and the methyl ester thereof, o-hydroxy-benzoic acid and the methyl ester thereof, 3-methyl-4-chlorophenol and the 3,5-dimethyl-4-chlorophenol, or a combination of two or more of said compounds. A particularly preferred cosolubiliser is p-hydroxy-benzoic acid methyl ester.

In the compositions of the invention the pharmaceutically acceptable salt of the anthracycline glycoside may be either a salt with inorganic acid such as, for instance, hydrochloric, hydrobromic, sulphuric or phosphoric acid, or a salt with an organic acid such as, for example, acetic, benzoic, maleic, fumaric, succinic, tartaric, citric, oxalic, glyoxylic, methanesulphonic, ethanesulphonic or benzenesulphonic acid. A particularly preferred salt is the salt with hydrochloric acid. In this specification a lyophilised injectable preparation is meant to be a lyophilised preparation leading, upon reconstitution, to a solution suitable for injection. The terms "pharmaceutical", "pharmaceutically" and the like are meant to refer to applications in both the human and the veterinary field. The terms "lyophilised" and "freeze-dried" are used without distinction.

While the main components of the lyophilised formulations of the invention are the anthracycline glycoside active drug substance and the above described cosolubilising agent, an inert excipient is usually present as a further component and it is, for example, lactose, mannitol, sorbitol or maltose, preferably lactose, in a suitable amount.

According to a particularly preferred feature of the invention a stable, rapidly soluble, lyophilised preparation is provided comprising doxorubicin hydrochloride as the active drug substance, p-hydroxy-benzoic acid methyl ester as the cosolubilising agent and the lactose as the inert excipient.

The relative proportions of the active drug substance and cosolubilising agent in the preparations of the invention are such that for 10 parts by weight of active drug substance about 0.1–10, preferably 0.5–2 parts by weight of cosolubilising agent may be present; a particularly preferred weight ratio between the cosolubiliser and the active drug substance is 1:10. The lyophilised formulations of the invention may contain the active drug substance in different amounts; typical formulations contain, for example, 5, 10, 20, 25 or 50 mg of anthracycline glycoside.

As already said, the presence of the cosolubilising agent in the lyophilised preparations of the invention enhances to a great extent the solubility of the drug so that the dissolution times in reconstitution. e.g. with physiological saline solution, are greatly reduced, even from about 2 minutes (for reconstitution of lyophilised formulations not containing solubility-enhancer) to 10–30 seconds or less.

The lyophilised formulations of the invention may be prepared in a conventional way following the usual freeze-drying techniques while taking, however, all precautions required in manipulation of toxic substances such as anthracycline glycosides. Thus, for example, the cosolubiliser, the anthracycline glycoside and the inert excipient are successively made to dissolve under stirring in a suitable amount of deaerated water for injections and then further water is added to reach the desired final volume. The resulting solution is clarified and filtered under sterile conditions and distributed in sterile containers (vials) of desired capacity. Freezing of the solution, e.g. at $-40°$ to $-50°$ C. for about 4 to 5 hours, and drying, e.g. at a final temperature of $40°-50°$ C. for about 6 to 7 hours, is then performed and the vials are sealed under sterile conditions according to usual procedure.

The dry unopened vials are completely stable for at least 3 months at 40° C. Also the reconstitution of the freeze-dried preparations, e.g. with sterile physiological saline solution, is carried out in conventional manner. Thus, for example, the physiological saline solution (0.9% sodium chloride aqueous solution) is used in a volume which may vary depending on the kind and on the amount of the active principle contained in the lyophilised cake: volumes from 5 ml to 25 ml of physiological saline solution may be, e.g., used for reconstituting amounts from 5 mg to 50 mg of anthracycline glycoside.

The reconstituted solutions of the invention have a pH which may vary between about 3 and about 6.5, depending particularly on the nature of the cosolubilising agent. Still further objects of the invention are the sterile solutions containing the anthracycline glycoside or salt thereof and the cosolubilising agent used for lyophilisation, (i.e. the solutions leading, by a freeze-drying process, to the lyophilised preparations of the invention) and the sterile injectable solutions obtained after reconstitution, particularly with physiological saline solution, of the lyophilised preparations of the invention, and their use in the treatment of a tumour in a human or animal host.

A further object of the invention is a method of producing an injectable solution of an anthracycline glycoside, characterised by dissolving, in a solution suitable for injection, particularly a physiological saline solution, a lyophilised preparation comprising the anthracycline glycoside, or a pharmaceutically acceptable salt thereof, and a cosolubilising agent which is a hydroxy-, mercapto- or amino-substituted benzoic acid or an alkali metal salt thereof or a $C_1$–$C_4$-alkyl ester thereof, or a ring-halogenated methyl-substituted phenol or an amino acid, or a combination of two or more of said compounds.

In addition the invention provides, as a still further object, a method of improving the solubility of an anthracycline glycoside in an injectable solution, particularly physiological saline solution, which comprises formulating the anthracycline glycoside with a cosolubilising agent according to the invention. Owing to the well-known anti-tumour activity of the anthracycline glycoside active drug substance the pharmaceutical compositions of the invention are useful for treating tumours on both human and animal hosts.

Examples of tumours that can be treated are, for instance, sarcomas, including osteogenic and soft tissue sarcomas, carcinomas, e.g. breast-, lung-, bladder-, thyroid, prostate- and ovarian carcinoma, lymphomas, including Hodgkin and non-Hodgkin lymphomas, neuroblastoma, Wilms tumour, and leukemias, including acute lymphoblastic leukemia and acute myeloblastic leukemia.

Examples of specific tumours that can be treated are Moloney Sarcoma Virus, Sarcoma 180 Ascites, Solid Sarcoma 180, gross transplantable leukemia, L 1210 leukemia and lymphocytic P 388 leukemia.

Thus, according to the invention there is also provided a method of inhibiting the growth of a tumour, in particular one of those indicated above, which comprises administering to a host suffering from said tumour an injectable solution obtained upon reconstitution of a lyophilised formulation according to the invention, containing the active drug substance in an amount sufficient to inhibit the growth of said tumour.

The injectable reconstituted solutions of the invention are administered by rapid intravenous injection or infusion according to a variety of possible dose schedules. Suitable dose schedule for doxorubicin may be, for example, of 60 to 75 mg of active drug substance per $m^2$ of body surface given as a single rapid infusion and repeated at 21 days; an alternative schedule may be of 30 mg/$m^2$ day by intravenous route for 3 days, every 28 days.

Suitable dosages for 4'-epi-doxorubicin and 4'-desoxy-doxorubicin may be, for instance, of 75 to 90 mg/$m^2$ and, respectively, of 25–35 mg/$m^2$ given in a single infusion to be repeated at 21 days.

Idarubicin, i.e. 4-demethoxy-daunorubicin, may be, e.g. administered intravenously at a single dose of 13–15 mg/$m^2$ every 21 days in the treatment of solid tumours, while in the treatment of leukemias a preferred dose schedule is, e.g., of 10–12 mg/m² day by intravenous route for 3 days, to be repeated every 15–21 days; similar dosages may be, e.g., followed also for daunorubicin.

The following Examples illustrate but do not limit in any way the invention.

EXAMPLE 1

Doxorubicin lyophilised formulations were prepared by the procedure reported below. The relative proportions of the various components employed in preparation were as hereinbelow indicated (amounts are per vial):

| | |
|---|---|
| doxorubicin.HCl | 10.00 mg |
| lactose.H₂O | 52.63 mg (equivalent to 50 mg of anhydrous lactose) |
| p-hydroxy benzoic acid methyl ester | 0.50 mg |
| water for injections | q.s. to 2.50 ml |

The p-hydroxy-benzoic acid methyl ester, the doxorubicin.HCl and the lactose were subsequently dissolved under stirring into water for injections, deaerated by nitrogen bubbling (about 90% of the finally required water volume). Deaerated water for injections was then added to get the final volume. The solution was clarified through a fibre-glass pre-filter and a 0.45μ microporous membrane, and then filtered under sterile conditions through a 0.22μ microporous membrane; the filtrate was directly collected in sterile area. Volumes of 2.5 ml of solution were automatically distributed, under sterile conditions, in sterile type III-colourless glass vials having 8/10 ml capacity.

The solutions were freezed in the vials at a temperature of −40° to −45° C. for 4 to 5 hours. Lyophilisation was then carried out, drying the product in the final stage at a 43°–45° C. temperature for 6 to 7 hours. Vials were closed with sterile chlorobutyl rubber stoppers and sealed with aluminium sterile caps.

By an analogous procedure, doxorubicin lyophilised formulations containing 20 mg of active drug substance were prepared from:

| | |
|---|---|
| doxorubicin.HCl | 20.00 mg |
| lactose.H₂O | 105.26 mg |
| p-hydroxy-benzoic acid methyl ester | 2.00 mg |
| water for injections | q.s. to 3.00 ml |

Freeze-drying was carried out in type III-glass vials of 20/26 ml capacity.

Again by an analogous procedure, doxorubicin freeze-dried formulations containing 50 mg of active drug substance were prepared from:

| | |
|---|---|
| doxorubicin.HCl | 50.00 mg |
| lactose.H₂O | 263.15 mg |
| p-hydroxy-benzoic acid methyl ester | 5.00 mg |
| water for injections | q.s. to 5.00 ml |

Freeze-drying was carried out in type III-glass vials of 50/57 ml capacity.

Doxorubicin lyophilised formulations analogous to those described above but containing p-hydroxy-benzoic acid or, respectively, p-amino-benzoic acid, or salicylic acid, or 3-methyl-4-chlorophenol or 3,5-dimethyl-4-chlorophenol or glycine, or cysteine or phenylalanine or proline, instead of p-hydroxy-benzoic acid methyl ester, were also prepared by analogous procedures. In particular, for example, formulations as follows were freeze-dried:

| 10 mg formulation | |
|---|---|
| doxorubicin.HCl | 10.00 mg |
| lactose.H₂O | 52.63 mg |
| p-hydroxy-benzoic acid methyl ester | 1.00 mg |
| water for injections | q.s. to 2.50 ml |

| 20 mg formulation | |
|---|---|
| doxorubicin.HCl | 20.00 mg |
| lactose.H₂O | 105.26 mg |
| p-hydroxy-benzoic acid | 2.00 mg |
| water for injections | q.s. to 3.00 ml |

Freeze-drying of these formulations was performed as reported before in this Example for formulations of same doxorubicin dosage.

The amounts indicated above and in the following Examples for the various components are amounts per vial.

EXAMPLE 2

Operating in analogous fashion as described in Example 1, 4'-epi-doxorubicin lyophilised formulations were prepared containing 10, 20 and 50 mg of active drug substance. The relative proportions of the various components employed in preparation were as indicated below.

| | 10 mg formulation | 20 mg formulation | 50 mg formulation |
|---|---|---|---|
| 4'-epi-doxorubicin.HCl | 10.00 mg | 20.00 mg | 50.00 mg |
| lactose.H₂O | 52.63 mg | 105.26 mg | 263.15 mg |
| p-hydroxy-benzoic acid methyl ester | 1.00 mg | 2.00 mg | 5.00 mg |
| water for injections | q.s. to 2.50 ml | q.s. to 3.00 ml | q.s. to 5.00 ml |

The three above formulations were freeze-dried as described in Example 1 in type III-glass vials having, respectively, 8/10 ml, 20/26 ml and 50/57 ml capacity.

Similar 4'-epi-doxorubicin freeze-dried formulations were also prepared, in analogous way, but containing a cosolubiliser chosen from p-hydroxy-benzoic acid, p-amino-benzoic acid, salicylic acid, 3-methyl-4-chlorophenol, 3,5-dimethyl-4-chlorophenol or glycine, or cysteine or phenylalanine or proline instead of p-hydroxy-benzoic acid methyl ester.

EXAMPLE 3

Following a procedure analogous to that described in Example 1, 4'-desoxy-doxorubicin lyophilised formulations were prepared containing 5 and 25 mg of active drug substance. The relative proportions of the various components employed in preparation were as indicated below:

|  | 5 mg formulation | 25 mg formulation |
| --- | --- | --- |
| 4'-desoxy-doxo-rubicin.HCl | 5.00 mg | 25.00 mg |
| lactose.H$_2$O | 52.63 mg | 263.15 mg |
| p-hydroxy-benzoic acid methyl ester | 0.50 mg | 2.50 mg |
| water for injections | q.s. to 2.00 ml | q.s. to 5.00 ml |

The two formulations were freeze-dried in accordance with the procedure of Example 1 in type III-glass vials having 8/10 ml and, respectively, 50/57 ml capacity.

Analogous lyophilised formulations were also prepared containing, however, p-hydroxy-benzoic acid or p-amino-benzoic acid or salicylic acid or 3-methyl-4-chlorophenol or 3,5-dimethyl-4-chlorophenol or glycine or cysteine or phenylalanine or proline, instead of p-hydroxy-benzoic acid methyl ester.

EXAMPLE 4

Proceeding in analogous fashion as reported in Example 1, lyophilised formulations containing daunorubicin (20 and, respectively, 50 mg of active drug substance) or 4-demethoxy-daunorubicin (5 and, respectively, 10 mg of active drug substance) were prepared. The relative proportions of the components in the various formulations were as reported below:

|  | 20 mg formulation | 50 mg formulation |
| --- | --- | --- |
| daunorubicin.HCl | 20.00 mg | 50.00 mg |
| mannitol | 100.00 mg | 250.00 mg |
| p-hydroxy-benzoic acid methyl ester | 2.00 mg | 5.00 mg |
| water for injections | q.s. to 3.00 ml | q.s. to 7.5 ml |

|  | 5 mg formulation | 10 mg formulation |
| --- | --- | --- |
| 4-demethoxy-daunorubicin.HCl | 5.00 mg | 10.00 mg |
| lactose.H$_2$O | 52.63 mg | 105.26 mg |
| p-hydroxy-benzoic acid methyl ester | 0.50 mg | 1.00 mg |
| water for injections | q.s. to 2.00 ml | q.s. to 3.00 ml |

Freeze-drying was performed in type I-glass vials for daunorubicin-containing formulations: vials of 10/14 ml capacity for 20 mg formulations and, respectively, vials of 50/57 ml/ capacity for 50 mg formulations were used. Type III-glass vials were used for freeze-drying 4-demethoxy-daunorubicin formulations: capacity of vials was 8/10 ml for 5 mg formulations and 20/26 ml for 10 mg formulations.

Analogous lyophilised preparations but containing p-hydroxy-benzoic acid or p-amino-benzoic acid or salicylic acid or 3-methyl-4-chlorophenol or 3,5-dimethyl-4-chlorophenol or glycine or cysteine or phenylalanine or proline instead of p-hydroxy-benzoic acid methyl ester, were also prepared.

EXAMPLE 5

Each lyophilised formulation obtained in the preceding Examples was reconstituted with physiological saline solution in the conventional manner. The volume of physiological saline solution used in reconstitution was dependent on the kind and on the amount of the active drug substance in the freeze-dried preparations. Thus, for example, freeze-dried preparations containing 10 mg of doxorubicin.HCl or 10 mg of 4'-epi-doxorubicin.HCl, as well as those containing 5 mg of 4'-desoxy-doxorubicin.HCl or 5 mg of 4-demethoxy-daunorubicin.HCl, were reconstituted with 5 ml of physiological saline solution.

Freeze-dried preparations containing 20 mg of doxorubicin.HCl or 20 mg of 4'-epi-doxorubicin.HCl or 10 mg of 4-demethoxy-daunorubicin.HCl or 20 mg of daunorubicin.HCl were reconstituted with 10 ml of physiological saline solution, while a volume of 25 ml of physiological saline solution was used to reconstitute lyophilised formulations containing 50 mg of doxorubicin.HCl or 50 mg of 4'-epi-doxorubicin.HCl or 50 mg of daunorubicin.HCl or 25 mg of 4'-desoxy-doxorubicin.HCl.

In all cases the reconstitution time was very short in that complete dissolution was observed in about 5-20 seconds, and, in any case, it did not require more than 30 seconds.

We claim:

1. A method of treating a tumor susceptible to doxorubicin therapy in a patient in need of such treatment, said method comprising administering to said patient a tumor growth-inhibiting amount of a sterile injectable solution comprising water, doxorubicin or pharmaceutically acceptable salt thereof and a cosolubilizing agent selected from the group consisting of a hydroxy-, mercapto-, or amino-substituted benzoic acid, an alkali metal salt thereof, a $C_1$-$C_4$ alkyl ester thereof, a ring-halogenated methyl-substituted phenol, an amino acid, and mixtures thereof, said solution being produced by reconstitution of a lyophilized preparation comprising doxorubicin or pharmaceutically acceptable salt thereof and said cosolubilizing agent.

2. Method of claim 1, wherein doxorubicin hydrochloride is administered to said patient.

3. Method of claim 1, wherein said cosolubilizing agent is selected from a group consisting of p-hydroxy-benzoic acid and the methyl ester thereof, p-amino-benzoic acid and the methyl ester thereof, o-hydroxy-benzoic acid and the methyl ester thereof, 3-methyl-4-chlorophenol and 3,5-dimethyl-4-chlorophenol.

4. Method of claim 1, wherein the cosolubilizing agent is p-hydroxy-benzoic acid methyl ester.

5. Method of claim 1, wherein the lyophilised preparation additionally includes an inert excipient.

6. Method of claim 5, wherein said inert excipient is lactose.

7. Method of claim 3, wherein said lyophilised preparation consists essentially of doxorubicin hydrochloride, p-hydroxy-benzoic acid methyl ester and lactose.

8. Method of claim 1, wherein the lyophilised preparation is reconstituted with physiological saline solution.

* * * * *